(12) United States Patent
Wang et al.

(10) Patent No.: US 7,485,760 B2
(45) Date of Patent: Feb. 3, 2009

(54) INTEGRATED HFC TRANS-1234ZE MANUFACTURE PROCESS

(75) Inventors: Haiyou Wang, Williamsville, NY (US); Hsueh Sung Tung, Getzville, NY (US); Yuon Chiu, Denville, NJ (US); Gustavo Cerri, Parsippany, NJ (US); Stephen A. Cottrell, Baton Rouge, LA (US)

(73) Assignee: Honeywell International Inc., Morristown, NJ (US)

( * ) Notice: Subject to any disclaimer, the term of this patent is extended or adjusted under 35 U.S.C. 154(b) by 107 days.

(21) Appl. No.: 11/657,354

(22) Filed: Jan. 24, 2007

(65) Prior Publication Data

US 2008/0051610 A1    Feb. 28, 2008

Related U.S. Application Data

(60) Provisional application No. 60/839,874, filed on Aug. 24, 2006.

(51) Int. Cl.
    *C07C 17/00*    (2006.01)
(52) U.S. Cl. ...................................... 570/236; 570/156
(58) Field of Classification Search .................. 570/156, 570/236
    See application file for complete search history.

(56) References Cited

U.S. PATENT DOCUMENTS

| 3,398,204 | A | * | 8/1968 | Gallant .................... 570/236 |
| 5,986,151 | A | | 11/1999 | Van Der Puy ............... 570/175 |
| 6,124,510 | A | | 9/2000 | Elsheikh et al. ............. 570/156 |
| 6,548,719 | B1 | | 4/2003 | Nair et al. ................... 570/157 |
| 2005/0013764 | A1 | * | 1/2005 | Merkel et al. ............... 423/488 |
| 2005/0020862 | A1 | | 1/2005 | Ting et al. ................... 570/164 |
| 2005/0090698 | A1 | | 4/2005 | Merkel et al. ............... 570/155 |

FOREIGN PATENT DOCUMENTS

| GB | 886716 A | 1/1962 |
| JP | 11140002 | 5/1999 |

* cited by examiner

*Primary Examiner*—Jafar Parsa
(74) *Attorney, Agent, or Firm*—Colleen D. Szuch

(57) ABSTRACT

An integrated process for the manufacture of HFO trans-1,3,3-tetrafluoropropene (HFO trans-1234ze) by first catalytically dehydrofluorinating 1,1,1,3,3-pentafluoropropane to thereby produce a mixture of cis-1,3,3,3-tetrafluoropropene, trans-1,3,3,3-tetrafluoropropene and hydrogen fluoride. Then optionally recovering hydrogen fluoride, catalytically isomerizing cis-1234ze into trans-1234ze, and recovering trans-1,3,3,3-tetrafluoropropene.

25 Claims, No Drawings

INTEGRATED HFC TRANS-1234ZE MANUFACTURE PROCESS

CROSS REFERENCE TO RELATED APPLICATION

This application claims the benefit of U.S. Provisional patent application Ser. No. 60/839,874 filed Aug. 24, 2006, which is incorporated herein by reference.

BACKGROUND OF THE INVENTION

The invention pertains to an integrated process for the manufacture of trans-1,3,3,3-tetrafluoropropene (HFO trans-1234ze). More particularly, the invention pertains to a process for the manufacture of the HFO trans-1234ze by first catalytically dehydrofluorinating 1,1,1,3,3-pentafluoropropane to thereby produce a mixture of cis-1,3,3,3-tetrafluoropropene, trans-1,3,3,3-tetrafluoropropene and hydrogen fluoride. Then optionally recovering hydrogen fluoride, catalytically isomerizing cis-1234ze into trans-1234ze, and recovering trans-1,3,3,3-tetrafluoropropene. The integration of an isomerization reactor charged with a suitable isomerization catalyst helps to convert cis-1234ze into its trans-isomer, which allows increasing the single-pass yield of trans-1234ze.

Chlorofluorocarbons (CFCs) like trichlorofluoromethane and dichlorodifluoromethane have been used as refrigerants, blowing agents and diluents for gaseous sterilization. In recent years, there has been widespread concern that certain chlorofluorocarbons might be detrimental to the Earth's ozone layer. As a result, there is a worldwide effort to use halocarbons which contain fewer or no chlorine substituents. Accordingly, the production of hydrofluorocarbons, or compounds containing only carbon, hydrogen and fluorine, has been the subject of increasing interest to provide environmentally desirable products for use as solvents, blowing agents, refrigerants, cleaning agents, aerosol propellants, heat transfer media, dielectrics, fire extinguishing compositions and power cycle working fluids. In this regard, trans-1,3,3,3-tetrafluoropropene (trans-1234ze) is a compound that has the potential to be used as a zero Ozone Depletion Potential (ODP) and a low Global Warming Potential (GWP) refrigerant, blowing agent, aerosol propellant, solvent, etc, and also as a fluorinated monomer.

It is known in the art to produce HFO-1234ze (i.e. HydroFluoroOlefin-1234ze). For example, U.S. Pat. No. 5,710,352 teaches the fluorination of 1,1,1,3-pentachloropropane (HCC-240fa) to form HCFC-1233zd and a small amount of HFO-1234ze. U.S. Pat. No. 5,895,825 teaches the fluorination of HCFC-1233zd to form HFC-1234ze. U.S. Pat. No. 6,472,573 also teaches the fluorination of HCFC-1233zd to form HFO-1234ze. U.S. Pat. No. 6,124,510 teaches the formation of cis and trans isomers of HFO-1234ze by the dehydrofluorination of HFC-245fa in the presence of an oxygen-containing gas using either a strong base or a chromium-based catalyst. European patent EP 0939071 describes the formation of HFC-245fa via the fluorination of HCC-240fa through intermediate reaction product which is an azeotropic mixture of HCFC-1233zd and HFO-1234ze.

It has been determined that these known processes are not economical relative to their product yield. It has also been noted that a significant amount of cis-1234ze is generated together with its trans-isomer in these know processes. Hence, there is a need for means by which trans-1234ze can be isolated from product mixtures and cis-1234ze can be either recycled via its fluorination to HFC-245fa or more preferably converted into trans-1234ze. Accordingly, the present invention provides an integrated process for producing trans-1234ze from which highly pure trans-1234ze can be obtained at a higher yield than prior art processes and cis-1234ze can be isomerized into trans-1234ze in contrast to known processes. In particular, it has now been found that trans-1234ze may be formed by dehydrofluorinating 1,1,1,3,3-pentafluoropropane in the absence of an oxygen-containing gas to produce a mixture of cis-1,3,3,3-tetrafluoropropene, trans-1,3,3,3-tetrafluoropropene and hydrogen fluoride. Then optionally, but preferably recovering hydrogen fluoride, catalytically isomerizing cis-1234ze into trans-1234ze, and then recovering trans-1,3,3,3-tetrafluoropropene. Unconverted cis-1234ze and HFC-245fa may then be directly recycled.

DESCRIPTION OF THE INVENTION

The invention provides a process for the production of trans-1,3,3,3-tetrafluoropropene which comprises:
(a) dehydrofluorinating 1,1,1,3,3-pentafluoropropane to thereby produce a result comprising cis-1,3,3,3-tetrafluoropropene, trans-1,3,3,3-tetrafluoropropene and hydrogen fluoride;
(b) optionally recovering hydrogen fluoride from the result of step (a);
(c) isomerizing at least a portion of the cis-1,3,3,3-tetrafluoropropene into trans-1,3,3,3-tetrafluoropropene; and
(d) recovering trans-1,3,3,3-tetrafluoropropene.

The invention also provides a continuous, integrated manufacturing process for the production of trans-1,3,3,3-tetrafluoropropene which comprises:
(a) dehydrofluorinating 1,1,1,3,3-pentafluoropropane conducted as a vapor phase reaction to thereby produce a result comprising cis-1,3,3,3-tetrafluoropropene, trans-1,3,3,3-tetrafluoropropene and hydrogen fluoride;
(b) recovering hydrogen fluoride from the result of step (a);
(c) isomerizing at least a portion of the cis-1,3,3,3-tetrafluoropropene into trans-1,3,3,3-tetrafluoropropene; and
(d) recovering trans-1,3,3,3-tetrafluoropropene.

The first step of the process involves the catalytic conversion of HFC-245fa by dehydrofluorinating HFC-245fa to produce a result comprising a combination of cis-1,3,3,3-tetrafluoropropene, trans-1,3,3,3-tetrafluoropropene and hydrogen fluoride. Dehydrofluorination reactions are well known in the art. Preferably dehydrofluorination of HFC-245fa is done in a vapor phase, and more preferably in a fixed-bed reactor in the vapor phase. The dehydrofluorination reaction may be conducted in any suitable reaction vessel or reactor, but it should preferably be constructed from materials which are resistant to the corrosive effects of hydrogen fluoride such as nickel and its alloys, including Hastelloy, Inconel, Incoloy, and Monel or vessels lined with fluoropolymers. These may be single pipe or multiple tubes packed with a dehydrofluorinating catalyst which may be one or more of fluorinated metal oxides in bulk form or supported, metal halides in bulk form or supported, and carbon supported transition metals, metal oxides and halides. Suitable catalysts non-exclusively include fluorinated chromia (fluorinated $Cr_2O_3$), fluorinated alumina (fluorinated $Al_2O_3$), metal fluorides (e.g., $CrF_3$, $AlF_3$) and carbon supported transition metals (zero oxidation state) such as Fe/C, Co/C, Ni/C, Pd/C. The HFC-245fa is introduced into the reactor either in pure form, impure form, or together with an optional inert gas diluent such as nitrogen, argon, or the like. In a preferred embodiment of the invention, the HFC-245fa is pre-vaporized or preheated prior to entering the reactor. Alternatively, the HFC-245fa is vaporized inside the reactor. Useful reaction temperatures may range from about 100° C. to about 600° C. Preferred temperatures may range from about 150° C. to about 450° C., and more preferred temperatures may range from about 200° C. to about 350° C. The reaction may be conducted at atmospheric pressure, super-atmospheric pressure or under vacuum. The vacuum pressure can be from about 5 torr to about 760 torr. Contact time of the HFC-245fa with the catalyst may range from about 0.5 seconds to about 120 seconds, however, longer or shorter times can be used.

In the preferred embodiment, the process flow is in the down or up direction through a bed of the catalyst. It may also be advantageous to periodically regenerate the catalyst after prolonged use while in place in the reactor. Regeneration of the catalyst may be accomplished by any means known in the art, for example, by passing air or air diluted with nitrogen over the catalyst at temperatures of from about 100° C. to about 400° C., preferably from about 200° C. to about 375° C., for from about 0.5 hour to about 3 days. This is followed by either HF treatment at temperatures of from about 25° C. to about 400° C., preferably from about 200° C. to about 350° C. for fluorinated metal oxide catalysts and metal fluoride ones or $H_2$ treatment at temperatures of from about 100° C. to about 400° C., preferably from about 200° C. to about 350° C. for carbon supported transition metal catalysts.

In an alternative embodiment of the invention, dehydrofluorination of HFC-245fa can also be accomplished by reacting it with a strong caustic solution that includes, but is not limited to KOH, NaOH, Ca(OH)$_2$ and CaO at an elevated temperature. In this case, the caustic strength of the caustic solution is of from about 2 wt. % to about 100 wt. %, more preferably from about 5 wt. % to about 90 wt. % and most preferably from about 10 wt. % to about 80 wt. %. The reaction may be conducted at a temperature of from about 20° C. to about 100° C., more preferably from about 30° C. to about 90° C. and most preferably from about 40° C. to about 80° C. As above, the reaction may be conducted at atmospheric pressure, super-atmospheric pressure or under vacuum. The vacuum pressure can be from about 5 torr to about 760 torr. In addition, a solvent may optionally be used to help dissolve the organic compounds in the caustic solution. This optional step may be conducted using solvents that are well known in the art for said purpose.

Optionally but preferably, hydrogen fluoride is then recovered from the result of the dehydrofluorination reaction. Recovering of hydrogen fluoride is conducted by passing the composition resulting from the dehydrofluorination reaction through a sulfuric acid extractor to remove hydrogen fluoride, subsequently desorbing the extracted hydrogen fluoride from the sulfuric acid, and then distilling the desorbed hydrogen fluoride. The separation may be conducted by adding sulfuric acid to the mixture while the mixture is in either the liquid or gaseous states. The usual weight ratio of sulfuric acid to hydrogen fluoride ranges from about 0.1:1 to about 100:1. One may begin with a liquid mixture of the fluorocarbons and hydrogen fluoride and then add sulfuric acid to the mixture.

The amount of sulfuric acid needed for the separation depends on the amount of HF present in the system. From the solubility of HF in 100% sulfuric acid as a function of a temperature curve, the minimum practical amount of sulfuric acid can be determined. For example at 30° C., about 34 g of HF will dissolve in 100 g of 100% sulfuric acid. However, at 100° C., only about 10 g of HF will dissolve in the 100% sulfuric acid. Preferably the sulfuric acid used in this invention has a purity of from about 50% to 100%.

In the preferred embodiment, the weight ratio of sulfuric acid to hydrogen fluoride ranges from about 0.1:1 to about 1000:1. More preferably the weight ratio ranges from about 1:1 to about 100:1 and most preferably from about 2:1 to about 50:1. Preferably the reaction is conducted at a temperature of from about 0° C. to about 100° C., more preferably from about 0° C. to about 40° C., and most preferably from about 20° C. to about 40° C. The extraction is usually conducted at normal atmospheric pressure, however, higher or lower pressure conditions may be used by those skilled in the art. Upon adding the sulfuric acid to the mixture of fluorocarbons and HF, two phases rapidly form. An upper phase is formed which is rich in the fluorocarbons and a lower phase which is rich in HF/sulfuric to acid. By the term "rich" is meant, the phase contains more than 50% of the indicated component in that phase, and preferably more than 80% of the indicated component in that phase. The extraction efficiency of the fluorocarbon can range from about 90% to about 99%.

After the separation of the phases, one removes the upper phase rich in the fluorocarbons from the lower phase rich in the hydrogen fluoride and sulfuric acid. This may be done by decanting, siphoning, distillation or other techniques well known in the art. One may optionally repeat the fluorocarbon extraction by adding more sulfuric acid to the removed lower phase. With about a 2.25:1 weight ratio of sulfuric acid to hydrogen fluoride, one can obtain an extraction efficiency of about 92% in one step. Preferably one thereafter separates the hydrogen fluoride and sulfuric acid. One can take advantage of the low solubility of HF in sulfuric at high temperatures to recover the HF from sulfuric. For example, at 140° C., only 4 g of HF will dissolve in 100% sulfuric acid. One can heat the HF/sulfuric acid solution up to 250° C. to recover the HF. The HF and sulfuric acid may then be recycled. That is, the HF may be recycled to a preceding reaction for the formation of the HFC-245fa and the sulfuric acid may be recycled for use in further extraction steps.

In another embodiment of the invention, the recovering of hydrogen fluoride from the mixture of fluorocarbon and hydrogen fluoride may be conducted in a gaseous phase by a continuous process of introducing a stream of sulfuric acid to a stream of fluorocarbon and hydrogen fluoride. This may be conducted in a standard scrubbing tower by flowing a stream of sulfuric acid countercurrent to a stream of fluorocarbon and hydrogen fluoride. Sulfuric acid extraction is described, for example in U.S. Pat. No. 5,895,639, which is incorporated herein by reference.

Alternatively, HF can be recovered or removed by using water or caustic scrubbers, or by contacting with a metal salt. When water extractor is used, the technique is similar to that of sulfuric acid. When caustic is used, HF is just removed from system as a fluoride salt in aqueous solution. When metal salt (e.g. potassium fluoride, or sodium fluoride) is used, it can be used neat or in conjunction with water. HF can be recovered when metal salt is used.

Then at least a portion of the cis-1,3,3,3-tetrafluoropropene is isomerized into trans-1,3,3,3-tetrafluoropropene. A stream of cis-1,3,3,3-tetrafluoropropene or its mixture with trans-1,3,3,3-tetrafluoropropene and/or 1,1,1,3,3-pentafluoropropane is fed into an isomerization reactor which contains a suitable isomerization catalyst (e.g., fluorinated metal oxides in bulk or supported, metal fluorides in bulk or supported, carbon supported transition metals, etc.) to convert most of the cis-1234ze into trans-1234ze. The isomerization reaction may be conducted in any suitable reaction vessel or reactor, but it should preferably be constructed from materials which are resistant to corrosion such as nickel and its alloys, including Hastelloy, Inconel, Incoloy, and Monel or vessels lined with fluoropolymers. These may be single pipe or multiple tubes packed with an isomerization catalyst which may be a fluorinated metal oxide, metal fluoride, or a carbon supported transition metal. Suitable catalysts non-exclusively include fluorinated chromia, chromium fluoride, fluorinated alumina, aluminum fluoride, and carbon supported cobalt. Useful reaction temperatures may range from about 25° C. to about 450° C. Preferred temperatures may range from about 50° C. to about 350° C., and more preferred temperatures may range from about 75° C. to about 250° C. The reaction may be conducted at atmospheric pressure, super-atmospheric pressure or under vacuum. The vacuum pressure can be from about 5 torr to about 760 torr. Contact time of the cis-1,3,3,3-tetrafluoropropene with the catalyst may range from about 0.5 seconds to about 120 seconds, however, longer or shorter times can be used.

Trans-1,3,3,3-tetrafluoropropene may be recovered from the reaction product mixture comprised of unreacted starting materials and by-products, including cis-1,3,3,3-tetrafluoropropene and any by-products and/or starting materials by any means known in the art, such as by extraction and preferably distillation. The mixture of trans-1,3,3,3-tetrafluoropropene, unconverted cis-1,3,3,3-tetrafluoropropene, unreacted HFC-245fa and any by-products are passed through a distillation column. For example, the distillation may be preferably conducted in a standard distillation column at atmospheric pressure, super-atmospheric pressure or a vacuum. Preferably the pressure is less than about 300 psig, more preferably less than about 150 psig and most preferably less than 100 psig. The pressure of the distillation column inherently determines the distillation operating temperature. Trans-1,3,3,3-tetrafluoropropene has a boiling point of about −19° C.; cis-1,3,3,3-tetrafluoropropene has a boiling point of about 9° C.; HFC-245fa has a boiling point of about 15° C. Trans-1,3,3,3-tetrafluoropropene may be recovered as distillate by operating the distillation column at from about −10° C. to about 90° C., preferably from about 0° C. to about 80° C. Single or multiple distillation columns may be used. The distillate portion includes substantially all the trans-1,3,3,3-tetrafluoropropene. The bottom stream of the distillation includes cis-1,3,3,3-tetrafluoropropene, HFC-245fa, a small amount of unrecovered HF and as well as any other impurities. Optionally, the residual amounts of HF/HCl present in the bottom distillate are removed by passing through a water/caustic scrubber, and followed by a sulfuric acid drying column. The bottom stream is then further distilled by using another distillation column. The mixture of cis-1234ze and HFC-245fa is recovered as a distillate, which is then recycled back to HFC-245fa dehydrofluorination reactor.

In the following alternative embodiments of the invention, the HFC-245fa dehydrofluorination reactor and the cis-1234ze isomerization reactor can be combined or independent. The trans-1234ze isolation can be after or before the cis-1234ze isomerization reaction.

Alternative 1:
(1) Combined reaction of HFC-245fa dehydrofluorination and cis-1234ze isomerization in one reaction vessel.
(2) Optional HF recovery.
(3) Isolation of trans-1234ze. Optionally, the remaining mixture is recycled back to step 1.

Alternative 2
(1) Catalytic dehydrofluorination of HFC-245fa into a composition comprising trans/cis-1234ze.
(2) Optional HF recovery.
(3) Isolation of trans-1234ze wherein the outlet stream of (2) feeds into a distillation column. The product, trans-1234ze, is isolated as a distillate from the rest of the mixture, i.e. cis-1234ze, the un-reacted HFC-245fa and other minor by-products. The residual amounts of HF/HCl present in the distillate are removed, and followed by a drying step. The bottom stream from the distillation of (3) is split to two streams and fed to steps (4) and (1), respectively. Optionally, further distillation is conducted by using another distillation column after step (3). In this distillation column, the mixture of cis-1234ze and HFC-245fa is recovered as a distillate, which is subsequently fed to step (4). The bottom stream from this $2^{nd}$ distillation column is recycled back to step (1).
(4) Catalytic isomerization of cis-1234ze.
The mixture of cis-1234ze/HFC-245fa from step (3) is fed into an isomerization reactor which contains a suitable isomerization catalyst to convert most of the cis-1234ze into trans-1234ze. The effluent from the catalytic reactor of step (4) is fed into step (3) for trans-1234ze isolation.

Alternative 3
(1) Catalytic dehydrofluorination of 245fa into trans/cis-1234ze.
(2) Optional HF recovery.
(3) Isolation of trans-1234ze
(4) Catalytic isomerization of cis-1234ze wherein the mixture comprising cis-1234ze and 245fa from step (3) is fed into an isomerization reactor which contains a suitable isomerization catalyst to convert most of the cis-1234ze into trans-1234ze.
(5) Isolation of trans-1234ze wherein the effluent from step (4) is fed into a distillation column. The product, trans-1234ze, is isolated as a distillate from the rest of the mixture, i.e. cis-1234ze, the un-reacted 245fa and other minor by-products. The bottom stream from the distillation of (5) is recycled back to step (1).

The following non-limiting examples serve to illustrate the invention.

EXAMPLE 1

HFC-245fa Dehydrofluorinaton Over Selected Catalysts

Three different kinds of catalysts, namely, fluorinated metal oxide, metal fluoride(s), and supported metal, were used for 245fa dehydrofluorination in Example 1. In each case, 20 cc of catalyst was used. A 100% 245fa feed was flowed over catalyst at a rate of 12 g/h. As shown in Table 1, all the catalysts listed in Table 1 exhibited a high activity (>80% 245fa conversion) and a high selectivity to cis/trans-1234ze (>90%) during 245 dehydrofluorination.

TABLE 1

| HFC-245fa dehydrofluorination over various catalysts | | | | | | |
|---|---|---|---|---|---|---|
| catalyst | temp ° C. | HFC-245fa conversion % | trans-1234ze selectivity % | cis-1234ze selectivity % | selectivity for others* % | trans-1234ze lbs/hr/ft$^3$ |
| Fluorinated Cr$_2$O$_3$ | 350 | 96.0 | 80.6 | 18.0 | 1.4 | 26.0 |

TABLE 1-continued

HFC-245fa dehydrofluorination over various catalysts

| catalyst | temp °C. | HFC-245fa conversion % | trans-1234ze selectivity % | cis-1234ze selectivity % | selectivity for others* % | trans-1234ze lbs/hr/ft$^3$ |
|---|---|---|---|---|---|---|
| AlF$_3$ | 350 | 96.8 | 80.4 | 16.3 | 3.3 | 26.2 |
| 10% MgF$_2$—90% AlF$_3$ | 350 | 98.3 | 78.6 | 17.5 | 4.0 | 26.0 |
| 0.5 wt % Fe/AC | 525 | 80.0 | 67.8 | 23.4 | 8.8 | 18.2 |

Reaction conditions: 20 cc catalyst, 12 g/h 245fa, 1 atm.
*Others include 2,3,3,3-tetrafluoropropene, 3,3,3-trifluoropropyne, etc.

EXAMPLE 2

Isomerization of cis-1234ze Over Selected Catalysts

Three different kinds of catalysts, namely, fluorinated metal oxide, metal fluoride(s), and supported metal, were used for cis-1234ze isomerization in Example 2. In each case, 20 cc of catalyst was used. A mixture of 85.3% cis-1234ze/14.7% 245fa was flowed over catalyst at a rate of 12 g/h. For a specified catalyst, a suitable reaction temperature was carefully chosen such that almost no dehydrofluorination reaction occurs to the HFC-245fa included in the feed. As shown in Table 2, all the catalysts except 0.5 wt % Co/AC listed in Table 2 provided a high activity (>80% cis-1234ze conversion) and a high selectivity to trans-1234ze (>95%) during cis-1234ze isomerization. The 0.5 wt % Co/AC catalyst exhibited a moderate activity (45% of cis-1234ze conversion) and a high selectivity to trans-1234ze (about 98%).

TABLE 2

Isomerization of cis-1234ze over various catalysts

| catalyst | reaction temp. (°C.) | conversion, % cis-1234ze | selectivity, % trans-1234ze |
|---|---|---|---|
| Fluorinated Cr$_2$O$_3$ | 100 | 91.0 | 100.0 |
| AlF$_3$ | 200 | 85.2 | 99.3 |
| 0.5 wt % Co/AC | 350 | 45.0 | 98.2 |

Reaction conditions: 20 cc catalyst, 12 g/h 85.3% cis-1234ze/14.7% 245fa, 1 atm

EXAMPLE 3

Cis-1234ze Isomerization in the Presence of HF Over Fluorinated Cr$_2$O$_3$

In this example, the product stream from Reactor 1 in which 245fa dehydrofluorination reaction was conducted over a fluorinated Cr$_2$O$_3$ catalyst at 350° C. was introduced into Reactor 2 which was also charged with a fluorinated Cr$_2$O$_3$ catalyst to conduct cis-1234ze isomerization reaction at 100 or 200° C. in the presence of HF (which was formed during 245fa dehydrofluorination in Reactor 1). Table 3 shows the compositions of exit gases of the two reactors. At 100° C., the mole percentage of trans-1234ze was slight higher in the exit gas of Reactor 2 than that in the exit gas of Reactor 1, while the mole percentage of cis-1234ze was slightly lower and the mole percentage of 245fa was about the same. As a result the mole ratio of trans-1234ze to cis-1234zw was slightly increased (e.g., from 3.96 to 4.36 after 1 h on stream) after isomerization reaction, indicating small amount of cis-1234 was converted into trans-1234ze through isomerization in Reactor 2. At 200° C., the mole percentages of both trans-1234ze and cis-1234ze were significantly lower in the exit gas of Reactor 2 than those in the exit gas of Reactor 1, while the mole percentage of 245fa was significantly higher. This indicates the occurrence of hydrofluorination reaction between c/t-1234ze and HF. These results suggest that the HF be preferably removed from the mixture before feeding into isomerization reactor in order to avoid the hydrofluorination of trans/cis-1234ze to 245fa and increase the conversion of cis-1234ze to trans-1234ze.

TABLE 3

The compositions of exit gases of the two reactors

| | | Rx 1 | | | | | Rx 2 | | | | |
|---|---|---|---|---|---|---|---|---|---|---|---|
| | | | mol, % | | | | | | mol, % | | |
| t (h) | Temp (°C.) | trans/cis ratio | trans-1234ze | cis-1234ze | HFC-245fa | others* | Temp (°C.) | trans/cis ratio | t-1234ze | c-1234ze | 245fa | others* |
| 1 | 350 | 3.96 | 69.3 | 17.5 | 3.2 | 10.0 | 100 | 4.36 | 70.5 | 16.2 | 3.2 | 10.1 |
| 2 | 350 | 3.94 | 71.7 | 18.2 | 2.5 | 7.6 | 100 | 4.22 | 72.5 | 17.2 | 2.4 | 7.8 |
| 3 | 350 | 3.87 | 73.1 | 18.9 | 2.1 | 5.8 | 100 | 4.25 | 73.7 | 17.3 | 2.1 | 7.0 |
| 4 | 350 | 3.86 | 73.2 | 19.0 | 2.2 | 5.6 | 200 | 6.06 | 55.2 | 9.1 | 29.4 | 6.3 |
| 5 | 350 | 3.86 | 73.3 | 19.0 | 2.2 | 5.2 | 200 | 5.94 | 38.2 | 6.4 | 51.8 | 3.6 |

*Others include 2,3,3,3-tetrafluoropropene, 3,3,3-trifluoropropyne, etc.

EXAMPLE 4

Combined HFC-245fa Dehydrofluorination and Cis-1234ze Isomerization

Two different kinds of catalysts, namely, fluorinated metal oxide and metal fluoride, were used for the combined reaction in Example 4. In each case, 20 cc of catalyst was used. A mixture of 8.2% of cis-1234ze/91.8% of HFC-245fa was flowed over catalyst at a rate of 12 g/h. For a specified catalyst, a suitable reaction temperature was carefully chosen such that both the HFC-245fa dehydrofluorination and the cis-1234ze isomerization can take place at the same time. The HFC-245fa conversion and trans-1234ze selectivity during the combined reaction was calculated assuming cis-1234ze remains unchanged before and after reaction. As shown in Table 4, the nominal trans-1234ze selectivity was about 94%, which was much higher than that in the reaction of HFC-245fa dehydrofluorination. This result indicates the occurrence of cis-1234ze isomerization to trans-1234ze during the combined reaction with cis-1234ze/HFC-245fa mixture as feed. This example demonstrated that under optimal operation temperature the HFC-245fa dehydrofluorination and the cis-1234ze isomerization can be conducted simultaneously over the same catalyst in the same reactor.

TABLE 4

Combined HFC-245fa dehydrofluorination and cis-1234ze isomerization

| catalyst | temp. (° C.) | HFC-245fa conversion, % | trans-1234ze selectivity, % | trans-1234ze lbs/hr/ft$^3$ |
|---|---|---|---|---|
| Fluorinated $Cr_2O_3$ | 250 | 77.5 | 93.5 | 22.5 |
| $AlF_3$ | 250 | 81.7 | 94.2 | 23.9 |

Reaction conditions: 20 cc catalyst, 12 g/h 8.2% cis-1234ze/91.8% HFC-245fa, 1 atm These examples demonstrate that the selected catalysts are, indeed, active for the dehydrofluorination of HFC-245fa to cis/trans-1234ze and the isomerization of cis-1234ze to trans-1234ze.

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. A process for the production of trans-1,3,3,3-tetrafluoropropene which comprises:
    (a) dehydrofluorinating 1,1,1,3,3-pentafluoropropane to thereby produce a result comprising cis-1,3,3,3-tetrafluoropropene, trans-1,3,3,3-tetrafluoropropene and hydrogen fluoride;
    (b) optionally recovering hydrogen fluoride from the result of step (a);
    (c) isomerizing at least a portion of the cis-1,3,3,3-tetrafluoropropene into trans-1,3,3,3-tetrafluoropropene; and
    (d) recovering trans-1,3,3,3-tetrafluoropropene.

2. The process of claim 1 further comprising the subsequent step of recovering cis-1,3,3,3-tetrafluoropropene, or a mixture of cis-1,3,3,3-tetrafluoropropene and 1,1,1,3,3-pentafluoropropane after step (d) and recycling cis-1,3,3,3-tetrafluoropropene or a mixture cis-1,3,3,3-tetrafluoropropene and 1,1,1,3,3-pentafluoropropane back to step (a) or step (a) and (c).

3. The process of claim 1 wherein the step of recovering hydrogen fluoride from the result of step (a) is conducted.

4. The process of claim 1 wherein steps (a) and (c) are conducted independently.

5. The process of claim 1 wherein steps (a) and (c) are combined and conducted as a single process step.

6. The process of claim 1 wherein step (d) is conducted after step (c).

7. The process of claim 1 wherein step (d) is conducted after step (a) but before step (c).

8. The process of claim 1 wherein step (d) is conducted after step (a) but before step (c); and then step (d) is then repeated after step (c).

9. The process of claim 1 wherein trans-1,3,3,3-tetrafluoropropene is recovered by distillation.

10. The process of claim 1 wherein step (d) is conducted by distilling the result of step (c) and recovering trans-1,3,3,3-tetrafluoropropene as a distillate and a residue comprising one or more of hydrogen fluoride, cis-1,3,3,3-tetrafluoropropene and 1,1,1,3,3-pentafluoropropane.

11. The process of claim 10 further comprising the subsequent step of removing hydrogen fluoride from the residue.

12. The process of claim 10 further comprising the subsequent step of removing hydrogen fluoride from the residue by passing the residue through a scrubber comprising water and a caustic, followed by a drying step.

13. The process of claim 10 further comprising the subsequent step of recovering at least one of cis-1,3,3,3-tetrafluoropropene and 1,1,1,3,3-pentafluoropropane from the residue and recycling at least one of the recovered cis-1,3,3,3-tetrafluoropropene and 1,1,1,3,3-pentafluoropropane back to step (a).

14. The process of claim 1 wherein the dehydrofluorinating is conducted as a vapor phase reaction.

15. The process of claim 1 wherein the dehydrofluorinating is conducted by reacting the 1,1,1,3,3-pentafluoropropane with a strong caustic solution.

16. The process of claim 1 wherein the dehydrofluorinating is conducted with a catalyst comprising one or more of fluorinated metal oxides, metal fluorides, in bulk form or supported and carbon supported transition metals.

17. The process of claim 1 wherein the recovering of hydrogen fluoride is conducted by passing the composition through a sulfuric acid extractor to remove hydrogen fluoride, subsequently desorbing the extracted hydrogen fluoride from the sulfuric acid, and then distilling the desorbed hydrogen fluoride.

18. The process of claim 1 wherein the isomerizing is conducted in an isomerizing reactor in the presence of an isomerizing catalyst.

19. The process of claim 1 wherein the isomerizing is conducted in an isomerizing reactor in the presence of an isomerizing catalyst comprising one or more of fluorinated metal oxides, metal fluorides, in bulk form or supported and carbon supported transition metals.

20. A continuous, integrated manufacturing process for the production of trans-1,3,3,3-tetrafluoropropene which comprises:
    (a) dehydrofluorinating 1,1,1,3,3-pentafluoropropane conducted as a vapor phase reaction to thereby produce a result comprising cis-1,3,3,3-tetrafluoropropene, trans-1,3,3,3-tetrafluoropropene and hydrogen fluoride;
    (b) recovering hydrogen fluoride from the result of step (a);

(c) isomerizing at least a portion of the cis- 1,3,3,3-tetrafluoropropene into trans-1,3,3,3-tetrafluoropropene; and (d) recovering trans-1,3,3,3-tetrafluoropropene.

21. The process of claim 20 wherein steps (a) and (c) are conducted independently.

22. The process of claim 20 wherein steps (a) and (c) are combined and conducted as a single process step before step (b).

23. The process of claim 20 wherein step (d) is conducted after step (c).

24. The process of claim 20 wherein step (d) is conducted after step (a) but before step (c).

25. The process of claim 20 wherein step (d) is conducted after step (a) but before step (c); and then step (d) is then repeated after step (c).

* * * * *

UNITED STATES PATENT AND TRADEMARK OFFICE
CERTIFICATE OF CORRECTION

PATENT NO. : 7,485,760 B2
APPLICATION NO. : 11/657354
DATED : February 3, 2009
INVENTOR(S) : Wang et al.

It is certified that error appears in the above-identified patent and that said Letters Patent is hereby corrected as shown below:

Col. 9, line 55 in Claim 1, in part (a) change "trails" to --trans--

Signed and Sealed this

Ninth Day of November, 2010

David J. Kappos
*Director of the United States Patent and Trademark Office*